(12) United States Patent
Dempster et al.

(10) Patent No.: US 6,202,468 B1
(45) Date of Patent: Mar. 20, 2001

(54) APPARATUS AND METHOD FOR THE DETERMINATION OF THE RELATIVE PROPORTIONS OF GASES

(75) Inventors: Philip Dempster, Concord; John Payne, Sacramento, both of CA (US)

(73) Assignee: Life Measurement Instruments, Concord, CA (US)

( * ) Notice: Subject to any disclaimer, the term of this patent is extended or adjusted under 35 U.S.C. 154(b) by 0 days.

(21) Appl. No.: 09/229,194

(22) Filed: Jan. 13, 1999

Related U.S. Application Data

(60) Provisional application No. 60/071,320, filed on Jan. 14, 1998.

(51) Int. Cl.[7] ............ G01N 19/10; G01N 29/02; G01N 31/00
(52) U.S. Cl. ................ 73/23.2; 73/24.01; 702/24
(58) Field of Search .................... 73/23.2, 24.01; 702/24; 204/425, 426, 427; 422/98; 374/117

(56) References Cited

U.S. PATENT DOCUMENTS

| | | | |
|---|---|---|---|
| 2,467,211 | 4/1949 | Hornfeck | 175/183 |
| 2,689,332 | 9/1954 | Greene | 324/36 |
| 3,049,665 | 8/1962 | Hummel | 324/36 |
| 3,720,870 | 3/1973 | Sueda | 324/34 R |
| 3,981,176 | * 9/1976 | Jacobs | 73/24.01 |
| 4,173,975 | 11/1979 | DeLong | 128/142 R |
| 4,280,183 | * 7/1981 | Santi | 702/24 |
| 4,432,226 | 2/1984 | Dempster | 73/27 A |
| 5,285,677 | * 2/1994 | Oehler | 73/24.01 |
| 5,325,703 | 7/1994 | Magori | 73/23.32 |
| 5,351,522 | 10/1994 | Lura | 73/24.01 |
| 5,823,044 | * 10/1998 | Logothetis | 73/23.2 |
| 5,831,145 | * 11/1998 | Logothetis | 73/23.2 |

* cited by examiner

Primary Examiner—Hezron Williams
Assistant Examiner—Jay L. Politzer
(74) Attorney, Agent, or Firm—Trial & Technology Law Group

(57) ABSTRACT

The present invention relates to a method of determining the relative proportions of gases in a mixture, such that the relative proportions of N gases are determined using N-1 sensors, not all of which are specific to a particular gas. In the preferred embodiment, oxygen and carbon dioxide are measured in the presence of nitrogen by measuring magnetic susceptibility and speed of sound. The described method of gas analysis leads to very fast response times and exceptional stability, making the technology suitable for breath-by-breath analysis of respired air. Notably, the method does not require high-temperature components, electrochemical cells, or consumable components.

12 Claims, 6 Drawing Sheets

APPARATUS AND METHOD FOR THE DETERMINATION OF THE RELATIVE PROPORTIONS OF GASES

CROSS REFERENCE TO RELATED APPLICATIONS

The present application is related to provisional patent application Ser. No. 60/071,320, filed Jan. 14, 1998 entitled "Metabolic/Pulmonary Measurement System", and the benefit of the earlier Jan. 14, 1998 filing date is claimed for the present application in accordance with 35 U.S.C. § 119 (e)(1).

BACKGROUND OF THE INVENTION

There are almost unlimited applications for the measurement of proportions of gases in a mixture. A particular example is rapid measurement of oxygen and carbon dioxide in the presence of nitrogen for evaluation of metabolic activity in humans or other organisms by indirect calorimetry. Other uses include general laboratory use, monitoring of combustion gases, and monitoring of green house gases.

Commonly, to determine the proportions of N gases in a mixture, N-1 sensors are used, each one specific to a particular gas. This usually implies a multiplicity of instruments and sample paths, in many cases the necessity of making multiple adjustments to equalize delays and response times of the various instruments, the expense of procuring multiple instruments, and the inconvenience of dealing with them. An exception to this is the mass spectrograph, but this instrument is expensive, bulky, and complex. The present invention relates to the measurement of N-1 physical or chemical parameters in a mixture of N gases in order to determine the relative proportions of N gases. The measurements do not need to be specific to a particular gas, but they must be linearly independent in order to provide unique solutions for the proportions of all the gases.

In particular, the invention relates to the measurement of oxygen and carbon dioxide in a mixture of oxygen, carbon dioxide, and nitrogen, by the measurement of the paramagnetic properties of the gas and the speed of sound of the gas. Desirable qualities of gas measurement include long term stability without readjustment, fast response time, low temperature, non-expendable sensor, ruggedness, and low cost relative to current technologies.

Commonly, oxygen is measured by (1) classical paramagnetic method (Pauling method), (2) zirconium fuel cell, (3) magnetic wind method, (4) acoustical methods based on modulated magnetic fields, and (5) wet chemical cell such as the Clark electrode. (1) suffers from slow response and is easily damaged by physical shock. (2) suffers from poor stability, high temperature, need for warm up, and a consumable cell which must be replaced at intervals. (3) suffers from slow response, interference by other gases, and unstable calibration. (4) appears promising, but has not enjoyed significant commercial success, possibly due to poor stability and interference by acoustical noise. (5) suffers from slow speed, depletion, and changing calibration.

The most prevalent method of measuring carbon dioxide is the measurement of infrared absorption. Such instruments work fairly well, but require relatively high temperatures, significant warm up, and frequent calibration.

As already pointed out, the combination of two separate gas sensing technologies to determine the proportional combination of three gases is a deficient method as regards to complication, cost, matching of delay times and response times.

PRIOR ART

Methods in which the flux of a magnetic circuit is modulated by changing the composition of a gas in a gap have been proposed for years. These systems can be divided into two classes. In one class, the gas in a gap is displaced by a moving object such as a toothed wheel or a nitrogen filled chamber on a piezoelectric bender. Such systems are described by Hornfeck, U.S. Pat. No. 2,467,211; Greene U.S. Pat. No. 2,689,332; Sueda U.S. Pat. No. 3,720,870; and Delong et al U.S. Pat. No. 4,173,975. In the other class, a test gas and a reference gas are made to replace each other by pneumatic means, such as valving or a moving diaphragm. Hummel has described such methods in U.S. Pat. Nos. 3,049,665, and 4,683,426.

The difficulty with such systems lies in the extremely weak flux changes produced, which make the systems subject to interference by external magnetic fields and vibration, and to irreducible electrical noise due to resistance of the sensing coils. Dempster described a system based on magnetic bridge methods in U.S. Pat. No. 4,432,226, which to some degree mitigated these problems, but which still was marginal with respect to vibration, external fields, and electrical noise.

The use of speed of sound measurement to determine gas composition has been used to determine the combination of a binary gas mixture (Magori U.S. Pat. No. 5,325,703, Lura U.S. Pat. No. 5,351,522), but the inventor is unaware of prior art in which the speed of sound is used in conjunction with another physical or chemical measurement in order to determine the relative combinations of three gases in a mixture.

A difficulty with speed of sound sensing as an analytic method is that changes in speed may be relatively slight, but dependency on temperature is strong and apparatus may introduce its own variable components. Therefore, designing a system with the requisite long term stability is challenging. It is a feature of the invention that a reference gas and a sample gas are rapidly interchanged in the measuring system, a comparison made between the two gases under virtually identical conditions. This method results in a system of unparalleled stability.

SUMMARY AND OBJECTS OF THE INVENTION

It is an object of the present invention to:
1) Provide a method to determine the specific proportions of N gases in a mixture using N-1 sensors, at least one of which is not specific to any of the gases.
2) Provide a method for the measurement of oxygen and carbon dioxide in the presence of nitrogen, in a single integrated analyzer.
3) Provide a method for the measurement of oxygen in the presence of a wide variety of gases.
4) Provide a method for the measurement of respiratory gases with very fast response time making it suitable for breath by breath analysis.
5) Provide a method for the measurement of respiratory gases with exceptional stability and instant warm up.
6) Provide a method for the rapid measurement of respiratory gases without high temperature components, electrochemical cells, or consumable components.

Other objects, features and advantages of the present invention will become apparent from the following detailed description when taken in conjunction with the accompanying drawings.

BRIEF DESCRIPTION OF THE DRAWINGS

The accompanying drawings, which are incorporated in and form a part of this specification, illustrate embodiments of the invention and, together with the description, serve to explain the principles of the invention.

DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

A. Gas Flow Circuit

Figure 1:
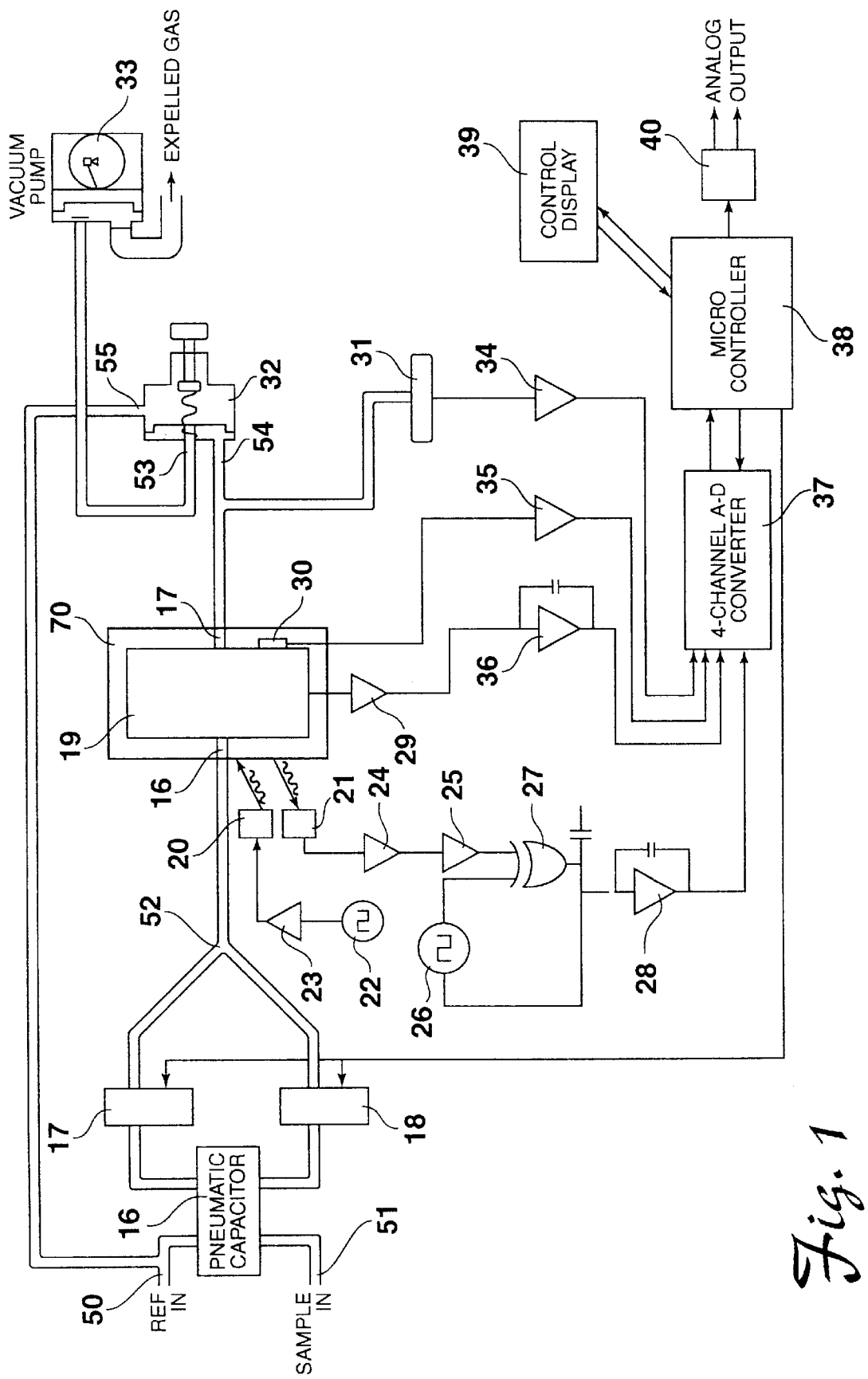
FIG. 1 shows a schematic representation of the entire system according to the present invention.

Referring to FIG. 1, there are two gas inlet tubes, 51 and 50, for the sample gas (gas being measured) and the reference gas (usually ambient air), respectively. These two inlets lead to a pair of electrically controlled valves 17 and 18 that are energized in complementary fashion. These valves alternately select the reference gas and the sample gas. One skilled in the art will recognize that a single three port valve could be substituted for the two single valves without changing the spirit of the invention.

Figure 4:
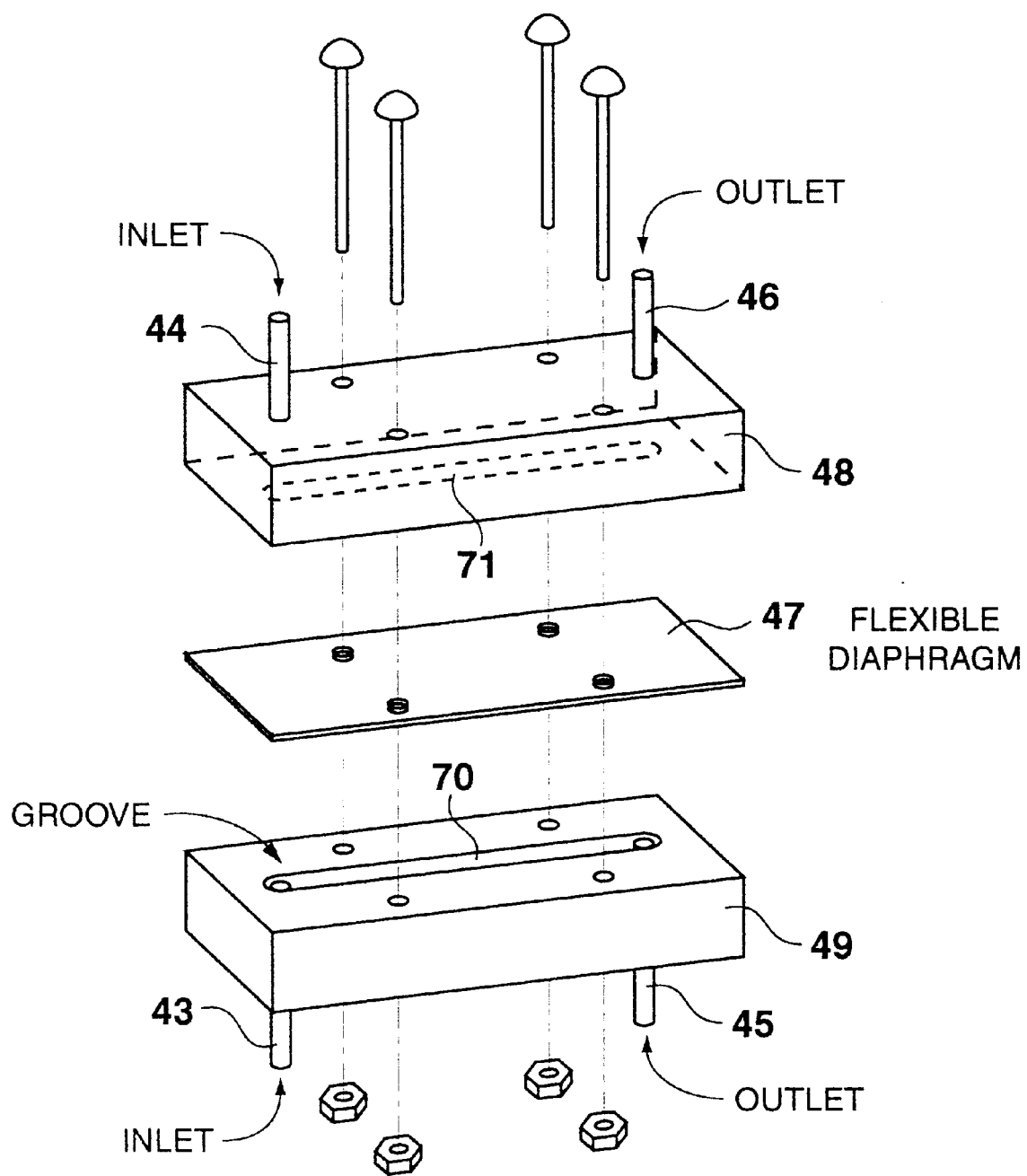
FIG. 4 shows an exploded view of an acoustic capacitor.

Still looking at FIG. 1, the two inlet tubes 50 and 51 are bridged by pneumatic capacitor 16 in the preferred embodiment. Turning to FIG. 4, the capacitor comprises two narrow passages 70 and 71 of similar cross section as the tubing, that are separated by a thin elastic membrane 47. The function of the membrane is to allow equalization of pressure fluctuations caused by the complementary opening and closing of the two valves. This reduces standing waves in any external sample tubes and reduces the pulsatile component of flow in these tubes. However the analyzer will work satisfactorily without this component, although with increased dependency on tube length. This description of the preferred embodiment is not intended to exclude devices not having a pneumatic capacitor.

It would also be possible to replace the pneumatic capacitor with two separate pneumatic compliances. In its simplest form these could consist of in-line volumes. The disadvantage would be slower response time of the instrument, but in many applications that would be of little consequence. In another form, these compliances could have elastic diaphragms or bellows type arrangements to reduce in-line volume.

Looking again at FIG. 1, the outlet of the two valves 17 and 18 leads to three-way junction 52 leading to inlet 16 of the test chamber in the combined oxygen and speed of sound sensor head (described below), preferably located adjacent to the inlet. It would also be practical to provide separate speed of sound and oxygen sensor heads in a series connection, but they are combined in the preferred embodiment. The speed of sound sensor could be omitted in order to construct an apparatus dedicated to the measurement of oxygen.

The outlet of the test chamber connects to spring-biased pneumatic comparator 32 which operates as a vacuum regulator. Input 53 (low pressure side) of the comparator goes to sampling pump 33. Reference port 55 of the comparator is connected to the reference input. Reference port 55 could be connected to ambient pressure, but in the preferred embodiment the input port is used so that if there is pressure drop in the reference line, the sampling vacuum will correspondingly increase, maintaining a constant pressure drop across the valves and the sensor head. As an alternative, input 53 could be connected to the sample input.

Various alternatives to the comparator are possible for pressure regulation. One alternative is a shunt, or blow-by regulator in which a spring or weight loaded valve opens when the vacuum exceeds a certain value. Such a system was described by Dempster in U.S. Pat. No. 4,432,226. Another alternative is to simply use a pump of reasonably stable characteristics, possibly introducing a restriction to limit flow. These are workable alternatives within the spirit of the invention, although they will not compensate for pressure drop in the sampling tubes. Another alternative involves using a variable drive to the pump in a servo control system utilizing a pressure transducer. A person skilled in the art would have no difficulty generating alternative scavenging pump systems which regulate to the pressure at the inlet to the reference port.

B. Combined Oxygen and Speed of Sound Sensor Head

Figure 2:
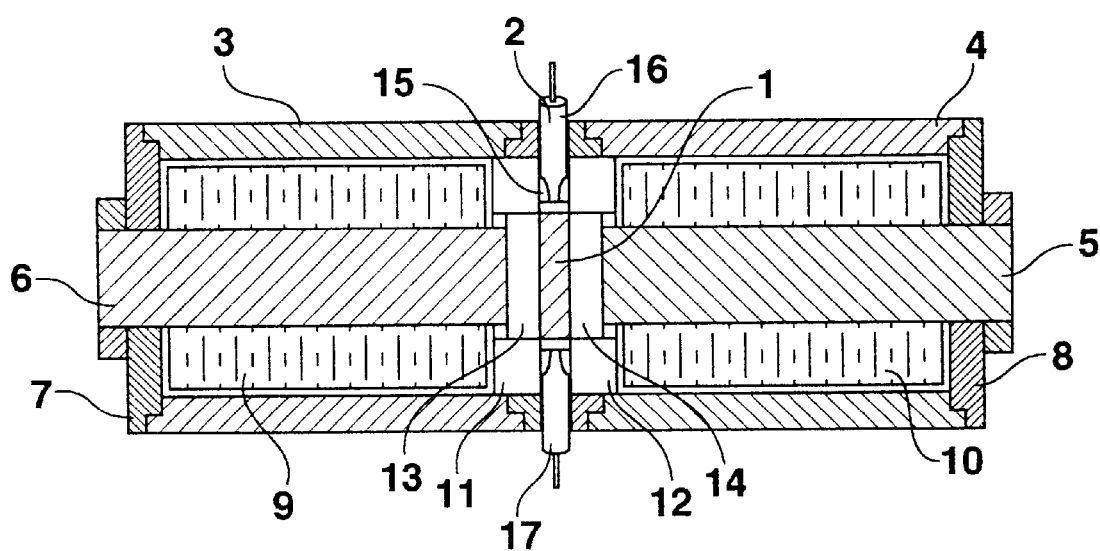
FIG. 2 shows a paramagnetic $O_2$ head which forms a portion of FIG. 1.
Figure 3:
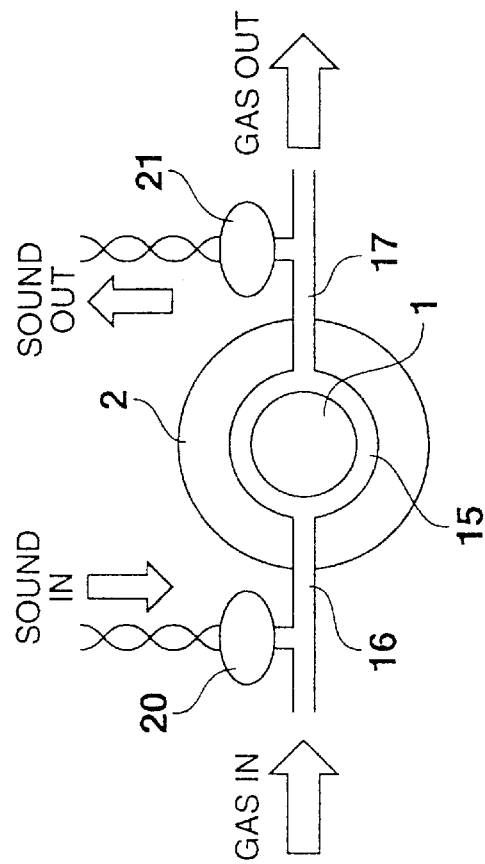
FIGS. 3A and 3B show a diagrammatic cross section of an annular test chamber with four ports and two ports.
Figure 3:
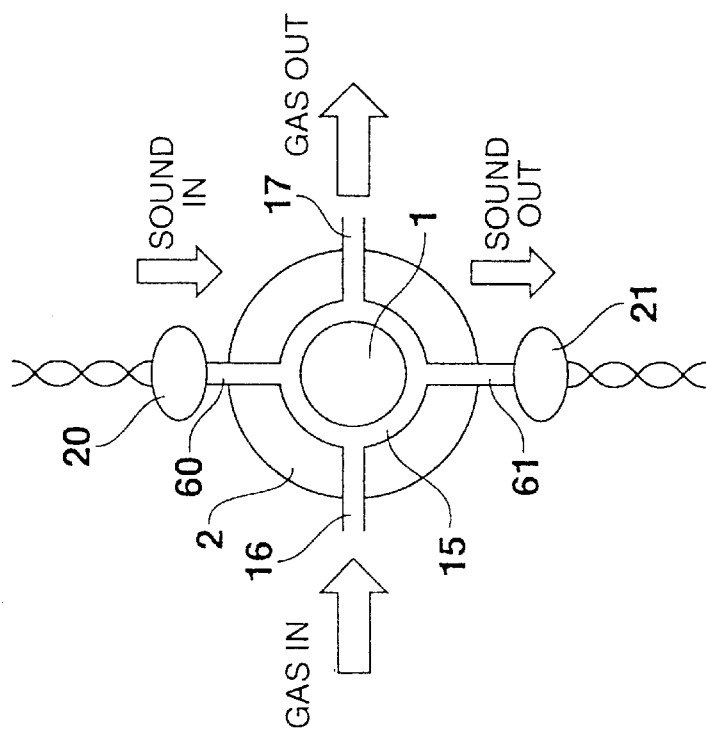

Now looking at FIGS. 2 and 3, the sensor head includes a disk shaped iron pole piece 1, surrounded by washer shaped pole piece 2, arranged so as to form an annular shaped chamber 15 whose sides are enclosed by non-magnetic, non-conductive washers 11 and 12, and through which gas may be passed by means of openings 16 and 17. There may be two additional ports, 60 and 61, arranged, at a 90 degree rotation from 16 and 17 which serve as ports for the sound transducers 20 and 21. To the center pole piece 1 are attached two magnets 13 and 14 so that the same poles (north or south) are facing each other through pole piece 1. Two complete magnetic circuits are formed by center structures 5 and 6, caps 7 and 8, and outer rings 3 and 4. Two coils, 9, and 10, are arranged over center structures 5 and 6, and confined by end caps 7 and 8 and outer rings 3 and 4.

The magnets 13 and 14 induce a magnetic field in the iron structures which passes through chamber 15. The field strength is dependent on the magnetic reluctance of this chamber, decreasing with greater reluctance and increasing with lesser reluctance. The reluctance of the chamber is decreased when it is filled with a magnetically susceptible gas such as oxygen relative to a nearly non-magnetic gas such as nitrogen. The flux changes caused by changing the gas in the chamber causes an induced electromotive force in the two coils, which is proportional to the time derivative of magnetic susceptibility of the gas in the chamber.

It will be noted that the two coils and magnetic circuits are arranged in mirror image symmetry. As a result, relative to signals caused by change in reluctance, signals caused by external magnetic fields will be out of phase with each other. The practical effect in the analyzer is that external magnetic interference tends to cancel out.

The use of two magnets on each side of the inner pole piece allows generation of high flux density with little saturated iron, in distinction to more conventional magnetic circuit layouts.

In general, geometrical deformation of a chamber whose walls are also pole pieces of the magnetic circuit will produce small changes in reluctance due to acoustical noise generated by the valves. Because the signal due to changes in magnetic susceptibility of the gases in the chambers is so small, this acoustic sensitivity may be quite significant. The use of a radially symmetrical chamber produces a balanced system of forces so that there is no net force that tends to cause a change in the geometrical relationship of the two pole pieces, virtually eliminating such effects in the invention.

Referring again to FIG. 1, preferably the combined paramagnetic and speed of sound head 19 is placed in magnetic shield 70, constructed of magnetically permeable material such as mu metal, in order to reduce the effects of external magnetic fields. It may have an active shield as described by Dempster in U.S. Pat. No. 4,432,226.

Looking now at FIG. 3, sound is generated by transducer 20, which may be a piezoelectric type. In the preferred embodiment, the sound enters the chamber through port 60, passes through the chamber and exits at port 61 where it is detected by another transducer 21, which acts as a microphone. Alternatively, sound may enter port 16 and leave by port 17, together with the sample and reference gases. There is a phase relationship between the input to transducer 20 and the output of transducer 21. This phase is a function of the speed of sound in annular chamber 15, and therefore responds to the composition of the gas in the chamber. Alternatively, a dedicated speed of sound head may be placed just ahead of or just behind a dedicated oxygen head. Such a head could be held at a constant temperature to insure stable operating characteristics.

C. Oxygen Electronics (i) Preamplifier

Figure 5:
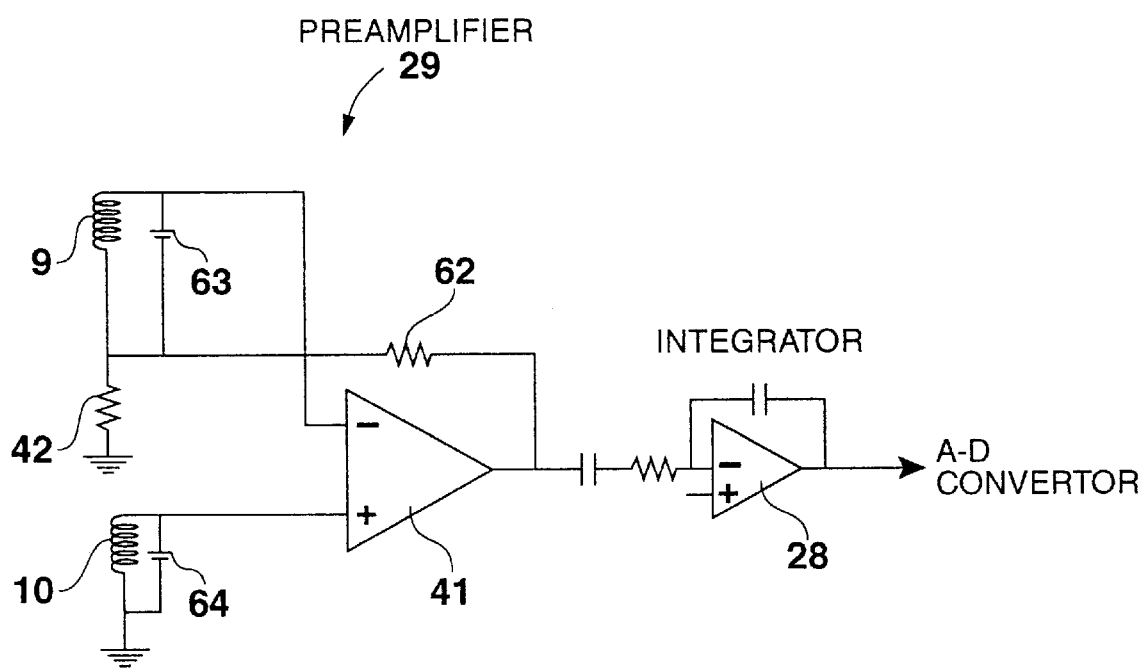
FIG. 5 shows an arrangement of analog electronics for a paramagnetic sensor.

Turning now to FIG. 5, the output of coils 9 and 10 in the oxygen sensor head is proportional to the time derivative of the magnetic susceptibility of the gas in the sample chamber. In a practical situation these signals are very small. Electrical noise due to resistance of the windings is significant. In such a situation, special attention must be paid to noise generated by the amplifier to which the coils are connected. The amplifier noise may be analyzed into two components, voltage noise and current noise. The latter is a factor if input impedance is greater than zero. The former is a factor if input voltage is low. Winding a coil with fine wire and many turns increases the signal to noise ratio for that part of the noise signal due to voltage noise, but decreases it for that part due to current noise. For a given amplifier and a given frequency spectrum, there will be an optimal input impedance that maximizes signal to noise ratio.

There are commercially available operational amplifiers that contribute less noise than that due to input resistance of the device being amplified. It is often the case with such amplifiers that there is a current noise that is common to both inputs and will be cancelled in the output if each input is connected to an identical impedance. In a simple conventional circuit, if the non-inverting input is used for the signal and the inverting for feedback, the feedback leg should have an impedance similar to the input device. However the non-identical current noise in the feedback leg will now add to system noise.

In the preferred embodiment, advantage is taken of the two coils to create an amplifier circuit in which there is no significant input impedance which is not signal generating, thereby creating an optimally low noise amplification system. The non-inverting input of amplifier 41 is connected to input coil 10 and the inverting input to coil 9. Whereas coil 10 is connected to ground, coil 9 is connected to ground through a resistance that is much smaller than the resistance of the coils. A proportion of the output signal of amplifier 41 is fed back to this point through resister 62. This feedback signal is conveyed to the non inverting input through coil 9. Each coil 9 and 10 is shunted by a small capacitor (63 and 64) which is insignificant at the frequencies of interest, to insure stability of the amplifier.

(ii) Further Analog Signal Processing

Still looking at FIG. 5, in the preferred embodiment the amplified signal is applied to integrator 28. The purpose of the integrator is to restore the derivative signal to an analog representation of magnetic susceptibility of the gas in the chamber. Now referring to FIG. 1, the integrated signal is then applied to the input of analog to digital converter 37, which is controlled and read by microcomputer 38, which also controls the valves and analyzes the digital representation of the output of integrator 28. The microcomputer 38 has attached to it appropriate control and visual monitoring functions 39. Digital to analog converter 40 provides analog outputs.

D. Speed of Sound Electronics

Figure 6:
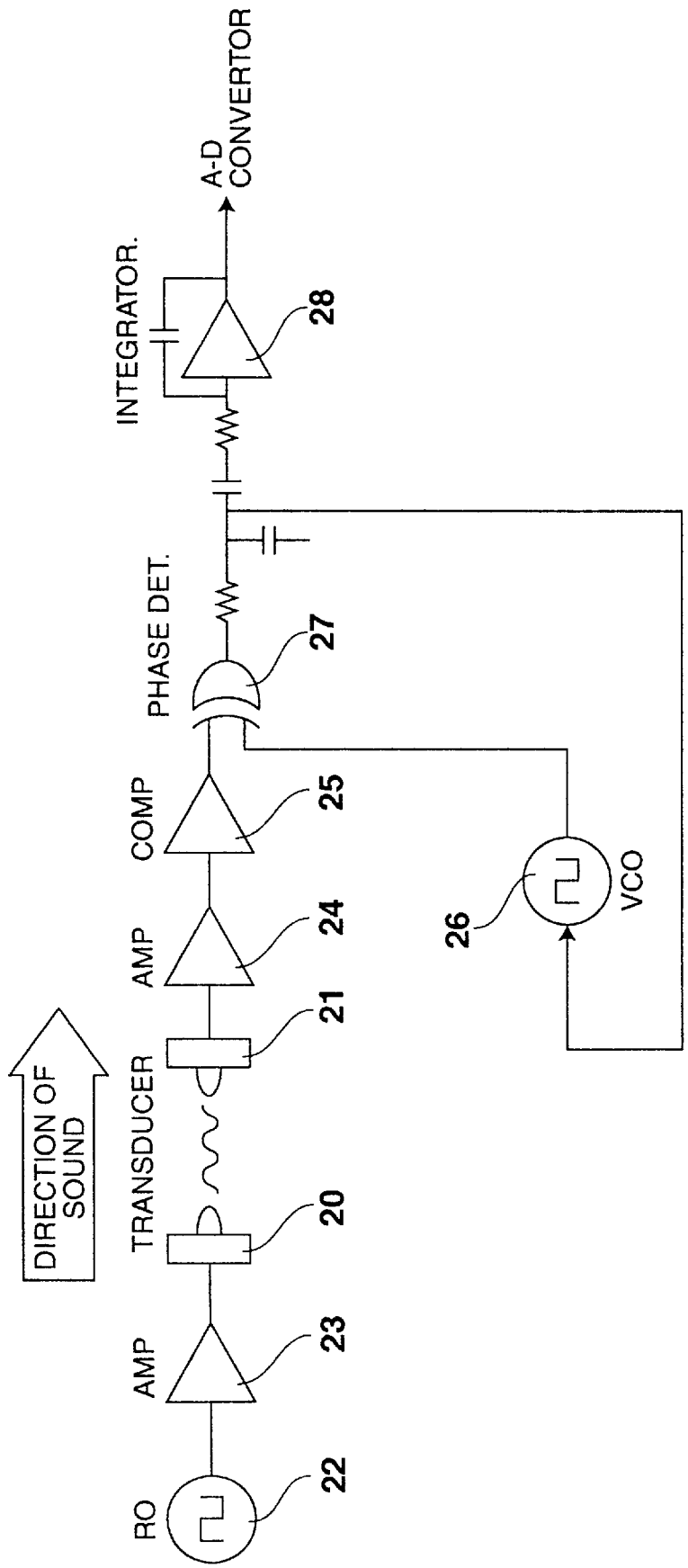
FIG. 6 shows an arrangement of analog electronics for the speed of sound sensor.

Referring to FIG. 6, in the preferred embodiment there is a fixed or reference oscillator (RO) 22, whose output is amplified by amplifier 23 and applied to transducer 20. The resulting sound wave is picked up by transducer 21 and amplified by amplifier 24. Amplifier 24 may include a filter to exclude frequencies different than that of oscillator 22. This amplified output is converted to a rectangular waveform by comparator 25. The output of voltage controlled oscillator 26 (VCO) is logically compared to the comparator output by an exclusive "or" gate 27. The output of the gate 27 is filtered and applied to the VCO, forming a classic phase-locked loop. The frequency of the VCO locks onto that of the RO 22.

If there is a change in the phase relationship of the sound output due to change in gas composition, the voltage at the input to the VCO will change momentarily in order to reestablish a phase relationship that results in a voltage at the input to the VCO that is appropriate to maintain the frequency relationship. The voltage at the input to the VCO is the time derivative of the phase relationship between the input and output of the speed of sound cell as comprised by the two transducers 20 and 21 and chamber 15 as shown in FIG. 3.

Referring back to FIG. 6, in the preferred embodiment the amplified signal is applied to integrator 28. The purpose of the integrator is to restore the derivative signal to an analog representation of the speed of sound of the gas in the chamber. The integrated signal is then applied to the input of the analog to digital converter 37 and dedicated microcomputer 38 shown in FIG. 1.

It would also be possible to directly compare the phase of oscillator 22 with the output of comparator 25, in order to generate a signal representative of speed of sound in the chamber. Such a system requires careful attention to the absolute phase relationship to insure linear operation.

E. Pressure and Temperature Acquisition

Still looking at FIG. 1, semiconductor temperature sensor 30 is attached to sensor head 19. Because of the small size of the passages and test chamber in sensor head 19, the surface area to volume ratio is high, and gases passing through the head are at substantial temperature equilibrium with sensor head 19.

Pressure transducer 31, which has a vacuum reference, is attached to outlet 17 of the sensor head. The pressure at this point is a close approximation to the pressure in the chamber.

The temperature and pressure signals are amplified and conditioned by amplifiers 35 and 34, respectively, and supplied to inputs of analog to digital converter 37.

F. Operation of the Analyzer

The controller includes a timer (not shown) that clocks operation. Referring to FIG. 1, valves 17 and 18 are operated in complementary fashion at a frequency that is preferably harmonically related to the power line frequency, for example 30 Hz. Pump 33 is caused to operate, establishing a partial vacuum at the outlet of the test chamber. When test valve 18 is open, the gas being measured is drawn into the chamber. When reference valve 17 is open, the reference gas, usually ambient air, is drawn into the chamber. Thereby the gas in the chamber is alternating between the gas under test and the reference gas at the frequency of valve operation.

The difference in magnetic susceptibility of the two gases causes a magnetic field variation in the two magnetic circuits, which induces a voltage in coils 9 and 10 (FIG. 2). This voltage is amplified and integrated in the analog electronics. The output of integrator 36 (FIG. 5) represents the fluctuating change of susceptibility of the gas in the chamber. This value is converted to a stream of digital numbers by the analog to digital converter 37. The frequency of conversion is many times the frequency of the valve so as to provide a good approximation to the waveform at the output of the integrator. The frequency may be 40 times higher, for example.

Looking at FIG. 6, the difference in speed of sound of the two gases causes phase variation in the output of sound transducer 21, which causes a fluctuating voltage at the input to VCO 26. This voltage is integrated by integrator 36. The output of integrator 36 represents the fluctuating change of speed of sound of the gas in the chamber. This value is converted to a stream of digital numbers by analog to digital converter 37 (FIG. 1). The frequency of conversion is many times the frequency of the valve so as to provide a good approximation to the waveform at the output of the integrator. Again, the frequency may be 40 times higher, for example.

Each of the two streams of numbers are multiplied by an internal digital sine wave function whose frequency is equal to that of the valve frequency. In setting up the instrument, the phase of the sine wave function for each number stream is adjusted so that when the test gas is oxygen and the reference gas ambient air, the products of the signals and the sine waves as summed over an integer number of cycles are maximums.

Two new streams of numbers are generated by summing exactly one cycle of sine wave signal products for each number stream. These streams may have a frequency double that of the valve frequency, although this is not an essential feature of the invention. The streams of numbers so generated represent the energies of the signals at valve frequency which are in phase with the corresponding sine wave. This is an effective method to reject spurious or random signal components. The streams of numbers may be filtered, if desired, by any one of a number of standard numerical methods.

The filtered stream of numbers corresponding to the magnetic susceptibility now may preferably be multiplied by the absolute temperature and divided by the barometric pressure to correct for density of the gas sample, in order to achieve maximum independence of ambient conditions. The stream may then be multiplied and offset by appropriate numbers under control of the user to provide a calibrated signal. The signal may be displayed by a digital display device such as an alpha numeric display or it may be converted to an analog signal by digital to analog converter 37 (FIG. 1).

The filtered stream of numbers corresponding to speed of sound may similarly be corrected for temperature. The speed of sound does not significantly depend on barometric pressure.

Using empirically derived data, a function relating speed of sound, oxygen concentration, and carbon dioxide concentration may be developed. This function may be applied to the two number streams in order to derive an output for carbon dioxide. The resulting stream may then be multiplied and offset by appropriate numbers under control of the user to provide a calibrated signal.

It should be recognized that analog integration and digital multiplication by sine wave is simply one method of generating an output signal that is responsive to the size and phase of the signals generated at the sensor head. As a minor example of a different method, integration of the analog signals could be accomplished in the digital realm. In another example, the average AC output voltages could be used. To a person skilled in the art, a number of alternative methods will suggest themselves. All of these embody the idea of measuring the strength of the signals from the head as a measure of difference in magnetic susceptibility and speed of sound of the test and reference gases.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. An apparatus for determining the relative proportion of gases within a gas mixture of three or fewer gases, including oxygen and carbon dioxide, the apparatus comprising:

means for determining the physical or chemical measure of the oxygen within a gas mixture to form a first measurement using a constantly applied magnetic field, means for determining the speed of sound within the gas mixture to form a second measurement, and means for determining the proportion of the carbon dioxide by numerical calculation from the first and second measurements.

2. The apparatus as in claim 1 including means for rapidly alternating a reference gas and a test gas through the apparatus, means for analyzing the resultant outputs for differences between the test and reference gas, and means for creating essentially continuous measurement streams based on these differences.

3. The apparatus as in claim 2 in which the oxygen measure is by paramagnetic measure.

4. The apparatus as in claim 3 including an oxygen measuring head and a speed of sound measuring head with a common measuring chamber.

5. The apparatus as in claim 4 in which the chamber is in the form of an annulus with a plurality of ports, two of which serve as an inlet and outlet for the gases, and two of which serve as inlet and outlet for sound transducers.

6. The apparatus as in claim 3 in which the oxygen measuring head and the speed of sound measuring head are arranged serially in a single measurement path.

7. The apparatus as in claim 3, in which alternation of the sample and reference gases is by periodic operation of one or more valves, and in which a pneumatic compliance is arranged between the two valve inlets.

8. The apparatus as in claim 3, in which gas is drawn through the apparatus by a low pressure source which includes a biased vacuum regulator, whose reference input is connected to one of the gas inlets.

9. An apparatus as in claim 3, in which the temperature of the sensor head is monitored and the monitored temperature is used in the calculation of the detected signals.

10. The apparatus as in claim 3, in which the absolute pressure in the sensor head is monitored and the monitored pressure is used in the calculation of the detected signal.

11. The apparatus as in claim 3 in which the resultant outputs are each synchronously multiplied by a periodic signal of the same frequency as the alternation of test and reference gases, to produce a detected signal based on differences between the test and reference gases.

12. The apparatus as in claim 3 in which the control means includes means for gathering data over a time period, calculating the detected signals over a multiplicity of phase relationships between the gas alternation and the periodic signal used in detection, and choosing and storing those phase relationships for each gas which give a maximum output for future use in the detection system.

* * * * *